United States Patent
Chen et al.

(10) Patent No.: US 10,457,596 B2
(45) Date of Patent: Oct. 29, 2019

(54) OPTICAL SENSOR EMPLOYING A REFRACTIVE INDEX ENGINEERED METAL OXIDE MATERIAL

(71) Applicants: UNIVERSITY OF PITTSBURGH—OF THE COMMONWEALTH SYSTEM OF HIGHER EDUCATION, Pittsburgh, PA (US); U.S. DEPARTMENT OF ENERGY, Pittsburgh, PA (US)

(72) Inventors: Peng Chen, Pittsburgh, PA (US); Jacob Lorenzi Poole, Pittsburgh, PA (US); Paul R. Ohodnicki, Allison Park, PA (US); Michael Paul Buric, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/873,049

(22) Filed: Jan. 17, 2018

(65) Prior Publication Data
US 2018/0141859 A1    May 24, 2018

Related U.S. Application Data

(62) Division of application No. 14/259,213, filed on Apr. 23, 2014, now abandoned.
(Continued)

(51) Int. Cl.
*C03C 25/106* (2018.01)
*G01N 21/05* (2006.01)
(Continued)

(52) U.S. Cl.
CPC ........ *C03C 25/106* (2013.01); *C03C 25/1061* (2018.01); *G01N 21/05* (2013.01); *G01N 21/553* (2013.01); *G01N 21/774* (2013.01)

(58) Field of Classification Search
CPC .. C03C 25/106; C03C 25/1061; G01N 21/774
See application file for complete search history.

(56) References Cited

U.S. PATENT DOCUMENTS

| 4,634,856 A | 1/1987 | Kirkham |
| 4,894,532 A | 1/1990 | Peterson et al. |

(Continued)

FOREIGN PATENT DOCUMENTS

| EP | 0120203 A1 | 1/1984 | |
| EP | 0120203 A1 * | 10/1984 | ........... G01N 21/783 |

*Primary Examiner* — Chris H Chu
(74) *Attorney, Agent, or Firm* — Eckert Seamans Cherin & Mellott, LLC (57) ABSTRACT

An optical sensor device includes an optical waveguide portion having a core, the core having a first refractive index, and a functional material layer coupled to the optical fiber portion, the functional material layer being made of a metal oxide material, the functional material layer being structured to have a second refractive index, the second refractive index being less than the first refractive index. The functional material layer may be a nanostructure material comprising the metal oxide material with a plurality of holes or voids formed therein such that the functional material layer is caused to have the second refractive index.

14 Claims, 5 Drawing Sheets

Related U.S. Application Data (60) Provisional application No. 61/816,457, filed on Apr. 26, 2013.

(51) Int. Cl.
*G01N 21/552* (2014.01)
*G01N 21/77* (2006.01)

(56) References Cited

U.S. PATENT DOCUMENTS

| | | | |
|---|---|---|---|
| 5,040,090 A | 8/1991 | Birkle et al. | |
| 5,319,975 A | 6/1994 | Pederson et al. | |
| 6,819,811 B1* | 11/2004 | Goldstein | B82Y 30/00 |
| | | | 385/12 |
| 6,952,436 B2 | 10/2005 | Wirnsberger et al. | |
| 7,037,554 B2 | 5/2006 | Tao et al. | |
| 7,349,600 B2 | 3/2008 | Chen | |
| 7,792,392 B2 | 9/2010 | Chen et al. | |
| 7,842,243 B2* | 11/2010 | Sarkisov | G01N 21/77 |
| | | | 356/128 |
| 2002/0065366 A1* | 5/2002 | Wirnsberger | C04B 26/14 |
| | | | 525/88 |
| 2003/0059150 A1* | 3/2003 | Lyons | G01F 1/661 |
| | | | 385/12 |
| 2004/0076391 A1* | 4/2004 | Ghoshal | G02B 1/046 |
| | | | 385/123 |
| 2004/0179765 A1* | 9/2004 | Kersey | G01B 11/18 |
| | | | 385/12 |
| 2005/0232532 A1* | 10/2005 | Wang | A61B 5/6892 |
| | | | 385/13 |
| 2008/0179063 A1* | 7/2008 | Smith | E21B 43/122 |
| | | | 166/335 |
| 2009/0289235 A1* | 11/2009 | Kniajanski | C07F 7/0836 |
| | | | 252/519.54 |
| 2010/0119194 A1* | 5/2010 | Seigler | B82Y 20/00 |
| | | | 385/32 |

* cited by examiner

OPTICAL SENSOR EMPLOYING A REFRACTIVE INDEX ENGINEERED METAL OXIDE MATERIAL

CROSS-REFERENCE TO RELATED APPLICATIONS

This is a divisional application which claims priority from U.S. patent application Ser. No. 14/259,213, filed on Apr. 23, 2014, entitled "Optical Sensor Employing a Refractive Index Engineered Metal Oxide Material," and under 35 U.S.C. § 119(e) to U.S. Provisional Patent Application No. 61/816,457, filed on Apr. 26, 2013, entitled "Fiber Optic Sensor Employing a Metal Oxide Material," the contents of which are incorporated herein by reference.

GOVERNMENT CONTRACT

This invention was made with government support under grant #1054652 awarded by the National Science Foundation and grant #DE-FE0003859 awarded by the Department of Energy. The government has certain rights in the invention.

BACKGROUND OF THE INVENTION

1. Field of the Invention

The present invention pertains to the integration of functional sensory materials with optical guiding structures by employing refractive index engineering through nano-structuring. More specifically, the present invention pertains to optical sensor devices, and, in particular, to an optical sensor device employing a metal oxide material such as a metal oxide material having a tailored refractive index through, for example, controlled nm-scale porosity.

2. Description of the Related Art

Optical fiber is one of the most versatile sensor platforms due to its inherent ability to operate in a wide array of extreme conditions. For example, fiber optic sensors can perform in a number of conditions/environments that are problematic and/or impossible for electronic sensors, such as, without limitation, high temperature environments, corrosive environments, strong electromagnetic field conditions, and in environments containing volatile organic/inorganic species.

As is known in the art, to perform chemical and/or bio sensing using fiber optic devices, such devices typically employ functional sensing materials that undergo material changes in response to the presence of an analyte, such as a given chemical species and/or biological material being sensed/detected. A variety of optical responses have been documented by exposing high refractive index sensing materials to a species of interest such as, but not limited to, optical effects in a sensing device due to a refractive index modulation, absorption, fluorescence, and optical losses due to coupling with surface plasmons.

Amongst their many applications, metal oxides are an important class of functional materials in chemical and bio sensing applications. A large variety of metal oxides have been explored extensively for highly sensitive resistance based electronic sensors. While the optimization of sensor responses to specific analytes remains a challenge, the basic origin and form of the resistivity response of metal oxide chemi-resistive sensors is well known and can be linked to a change in free carrier concentration or free carrier mobility.

In contrast, the exploration of metal oxides in optical sensing applications (e.g., as coatings on optical fibers) has not been effectively investigated due in part to the incompatibilities of the refractive indices of metal oxides and optical fiber components, such as silica fiber cores. The refractive index is arguably one of the most important parameters in optics as it determines the working relationships between the constituent components of optical devices. In particular, in an optical sensing application employing a metal oxide as a functional material, the sensitivity to an analyte is a key issue. One way to improve the sensitivity of a fiber optic sensor for a given metal oxide coating is to increase the interaction length between the metal oxide coating and the guided light, which in turn facilitates the accumulation of the response, whether refractive index or absorption based, leading to an increase in sensitivity. This is, however, not a trivial issue since the typical refractive index, n, of a metal oxide (n≥2.0) is significantly higher than that of commercial silica fiber cores (n~1.46). As a result, the interaction between the guided light in the core of a silica fiber with higher index sensing can destroy the guiding of the fiber due to scattering or radiative losses if the design restrictions imposed by the high refractive indices are not considered. To date, the only way to overcome this problem, with some degrees of success, is to utilize very thin film coatings when they are in close proximity with the fiber core. Such thin coatings reduce the amount of the evanescent waves confined in the film, and thus reduce the sensitivity of the device (due to a reduction of the interaction length to both the analyte and the interrogating field).

SUMMARY OF THE INVENTION

In one embodiment, an optical sensor device is provided that includes an optical waveguide portion having a core, the core having a first refractive index, and a functional material layer coupled to the optical waveguide portion, the functional material layer being made of a metal oxide material, the functional material layer being structured to have a second refractive index, the second refractive index being less than the first refractive index. In the exemplary embodiment, the functional material layer is a nanostructure material comprising the metal oxide material with a plurality of holes or voids formed therein such that the functional material layer is caused to have the second refractive index.

In another embodiment, a method of making an optical sensor device is provided that includes providing an optical waveguide portion having a core, and foaming a functional material layer made of a metal oxide material, the functional material layer being coupled to the optical waveguide portion, the core having a first refractive index, the functional material layer being structured to have a second refractive index, the second refractive index being less than the first refractive index.

In still another embodiment, an optical sensor device is provided that includes a multilayer hollow waveguide device having: (i) a hollow waveguide tube layer, (ii) an intermediate layer provided inside the hollow waveguide tube layer, and (iii) a metal oxide coating layer inside the intermediate layer.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "metal oxide" shall mean a chemical compound that contains at least one oxygen atom and at least one other element in the form of a metal in its chemical formula, and shall include doped variants thereof and mixed metal oxides. Examples of metal oxides are, without limitation, zeolites, $SnO_2$, TiO2, ZnO, $WO_3$, and perovskites such as barium strontium cobalt iron oxide (BSCF).

As used herein, the term "nanostructure" shall mean an object of intermediate size between microscopic and molecular structures having at least one dimension (e.g., the diameter of a hole, a sphere or a tubular structure) that is much less than the wavelength of the light used (e.g., typically less than one order of magnitude defined as 1/10, not excluding functional designs which may be less strict such as 1/5th). For example, in one particular embodiment, the at least one dimension is ≤100 nm.

As used herein, the term "sol-gel process or method" shall mean a method for producing solid materials from small molecules (e.g., used for the fabrication of metal oxides, especially the oxides of silicon and titanium), that includes conversion of monomers into a colloidal solution (sol) that acts as the precursor for an integrated network (or gel) of either discrete particles or network polymers.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
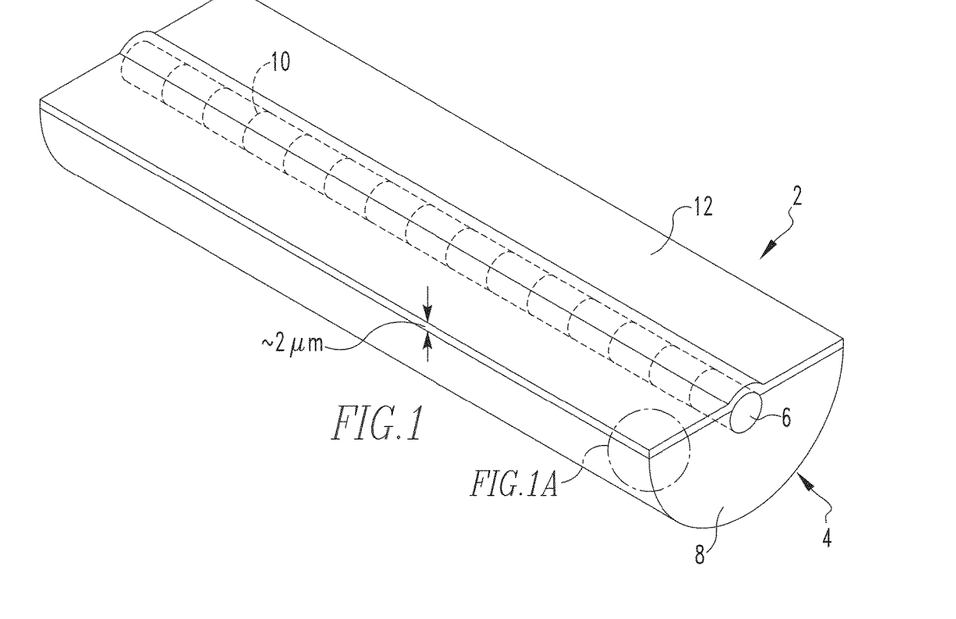
FIG. 1 is a schematic diagram of a fiber optic sensor device according to an exemplary embodiment of the present invention.
Figure 1A:
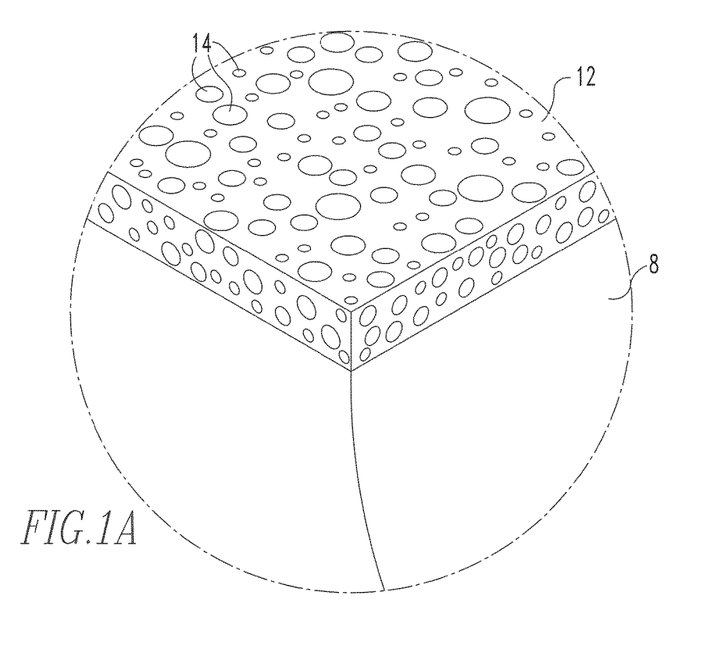
FIG. 1A is a magnified view of a portion of the fiber optic sensor device of FIG. 1.
Figure 2:
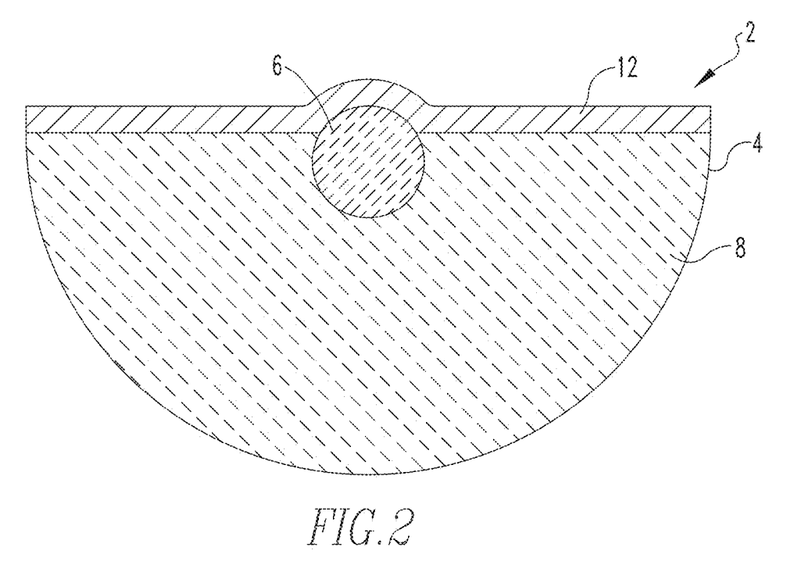
FIG. 2 is a cross-sectional diagram of the fiber optic sensor device of FIG. 1.

FIG. 1 is a schematic diagram and FIG. 2 is a cross-sectional diagram of a fiber optic sensor device 2 according to an exemplary embodiment of the present invention. FIG. 1A is a magnified view of a portion of fiber optic sensor device 2. As described in detail below, fiber optic sensor device 2 employs a metal oxide functional material having a tailored refractive index, and is structured to detect/measure an analyte, such as a gas (e.g., without limitation, $NH_3$), in an environment based on a change in the refractive index of the functional material induced by an analyte, a change in the optical absorption of the functional material induced by an analyte, a change in the fluorescent properties, or some combination of the above mentioned types of response. Fiber optic sensor device 2 in the non-limiting exemplary embodiment includes a D-shaped optical fiber 4 having a core 6 surrounded by a cladding layer 8 which has a hemispherical cross-section. It will be understood, however, that such a D-shaped optical fiber is meant to be exemplary only, and that optical fibers having other shapes, such as a fiber having a cylindrical cross-section, are contemplated within the scope of the disclosed concept. It will also be understood that optical waveguide structures not in the form of an optical fiber are a natural extension of the embodiments described herein and are contemplated within the scope of the disclosed concept. In the exemplary embodiment, core 6 has a cylindrical shape, but it will be appreciated that other shapes, such as a shape having an elliptical cross-section, are also possible. Core 6 and cladding layer 8 are each made of a light propagating material, such as fused silica (possibly doped with another material such as germanium and/or boron), wherein core 6 has an index of refraction that is greater than the index of refraction of cladding layer 8. In the exemplary embodiment, D-shaped optical fiber 4 is formed in manner wherein the top portion (e.g., top quarter to half) of core 6 extends beyond and above the top, flat edge of cladding layer 8 (i.e., without coating layer 12 described below, the top portion of core 6 is exposed).

D-shaped optical fiber 4 in the exemplary embodiment also includes an in-fiber optic component 10 formed in core 6. In the exemplary embodiment, in-fiber optic component 10 is a Fiber Bragg Grating (FBG). As is known in the art, an FBG consists of a series of perturbations, foaming a grating, in the index of refraction along the length of an optical fiber. An FBG reflects a spectral peak of a light that is transmitted through the fiber, and the particular spectral peak (called the resonance wavelength) that is reflected depends upon the grating spacing. In the exemplary embodiment, in-fiber optic component 10 is an FBG with a constant period (meaning the grating elements are evenly spaced), referred to as a uniform FBG. In-fiber optic component 10 may also take on other forms, such as an FBG having gratings that have a varying period (referred to as a chirped FBG), a fiber interferometer, or a Fabry-Perot cavity (FP). It will be understood, however, that in-fiber optic component 10 formed in core 6 is optional, and that fiber optic sensor device 2 may also be formed with a D-shaped optical fiber 4 that does not include an in-fiber optic component 10.

As seen in FIGS. 1, 1A and 2, in the exemplary embodiment, fiber optic sensor device 2 further includes a coating layer 12 provided on the top, flat surface of cladding layer 8 and the top portion core 6. In an alternative embodiment, coating layer 12 may be provided on the entire outer perimeter of fiber optic sensor device 2. Coating layer 12 is made of a metal oxide material and is structured and formed in a manner such that coating layer 12 has a refractive index that is less than the refractive index of core 6. In the exemplary, non-limiting embodiment, the refractive index of coating layer 12 is about 99.0% to about 99.7% of the refractive index of core 6. In one particular exemplary embodiment, core 6 is made of fused silica having a refractive index of about 1.46, and coating layer 12 is made of $SnO_2$ (which, in its normal form typically has a refractive index of about 2.2) and is structured and formed such that it has a refractive index of about 1.45. In another particular exemplary embodiment, core 6 is made of fused silica having a refractive index of about 1.468, and coating layer 12 is made of $SnO_2$ (which, in its normal form typically has a refractive index of about 2.2) and is structured and formed such that it has a refractive index of about 1.461. In the exemplary embodiment, and as shown schematically in FIG. 1A, coating layer 12 is structured and formed to have such a reduced refractive index by forming coating layer 12 as a highly porous nanostructure material with a plurality of voids (also referred to as holes) 14 (i.e., nano-voids or nano-holes) formed therein (sometimes referred to as a network of voids 14). In the illustrated exemplary embodiment, coating layer 12 is about 2 μm thick and, with the voids 14 formed therein, is about 60% void and about 40% $SnO_2$. (the percentage or fraction of voids 14 as compared to the volume of the whole structure being referred to herein as the "total volume fraction of voids"). It will be understood, however, that by employing the design method described herein, virtually any thickness of coating layer 12 may be employed. In the exemplary embodiment, the total volume fraction of voids in coating layer 12 is chosen so as to cause coating layer 12 to have an "engineered" refractive index that is less than the refractive index of core 6

In one particular, non-limiting embodiment, coating layer 12 is formed such that it has a lattice structure wherein the voids 12 have a generally regular and consistent shape (such as a spherical shape). In one such lattice structure, the voids 14 have a characteristic dimension (e.g., width or diameter) of the void network that is less than or equal to a predetermined value. For example, and without limitation, the voids 14 may be spherical and each have a diameter of about 20 nm, of between about 10 nm and about 20 nm, of about ≤20 nm, of between about 10 nm and about 50 nm, or of between about 10 nm and about 100 nm. It will be understood that these dimension are meant to be exemplary only and that it is possible for the void sizes to be much larger, perhaps up to even 200 nm, and still be viable for engineering the refractive index for light at 1550 nm. In still another example, the voids 12 may actually be a continuous network and the characteristic dimension (e.g., 20 nm size) may be the characteristic width of the void network in one dimension.

In one particular embodiment, characteristic dimension of the void network is chosen so that local light scattering is avoided/minimized by making the characteristic dimension of the voids 14 at least about ten times smaller than the wavelength of the light being used/measured in any particular application.

The controlled tailoring (via controlled nano-structuring) of the metal oxide porosity as just described is what allows the refractive index of coating layer 12 to be reduced below that of core 6, which in turn enables the development of highly sensitive evanescent wave fiber optic sensors with long interaction lengths. At the same time, it removes the thickness, interaction length, and proximity restrictions that have previously been imposed in the prior art by the high refractive indices of metal oxide materials.

In addition, in further embodiments, metal oxide coating layer 12 may be modified through doping or by forming a mixed metal oxide to target fiber optic sensor device 2 for a particular gas species of interest. For example, and without limitation, coating layer 12 may be made of $SnO_2$ as described herein and may be doped with palladium (Pd) or platinum (Pt) in order to target fiber optic sensor device 2 for hydrogen (H) sensing. In another embodiment, the coating layer may be a hybrid metal oxide that contains a mixture of two or more materials. For example, and without limitation, tin oxide with zinc oxide.

In one particular exemplary embodiment, a polymer-based synthesis technique is employed to form fiber optic sensor device 2 having coating layer 12 such that, as just described, it has a tailored refractive index that is less than the refractive index of core 6. More specifically, a sol-gel approach is used to produce coating layer 12 over D-shaped optical fiber 4. In this sol-gel approach, a polymer additive is used as a structure directing agent such that the porosity of the metal oxide ($SnO_2$ in the illustrated exemplary embodiment) is controlled at the scale of tens of nanometers for refractive index tailoring. The porosity/refractive index is controlled by varying the included amount of the polymer. In the exemplary embodiment, poloxamer 407, also known by the trade name Pluronic® F127, a triblock copolymer, is used as the structure directing agent. During the process, the structure directing agent is mixed with $SnCl_4$ in Ethanol to form a precursor. The precursor is then modified by the addition of HCl to adjust the pH to about 0.5 (in the exemplary embodiment, precursor is modified by the addition of 37% HCl dissolved in water). Other chemicals could be used for such purposes as well. For example, refractive index tailored $SnO_2$ films can also be synthesized by addition of a structure directing agent to a mixture of Sn-isopropoxide and a solvent such as a mixture of isopropanol and toluene among many others. Other acids could include glacial acetic acid, nitric acid, and many others. Also, metal oxides can be coated by non-wet processing, such as sputtering, where the nm-scale voids could be fabricated through nano-lithography and patterning approaches, reactive ion-etching, or other suitable techniques. Other exemplary embodiments include: (i) TiO2 solutions containing TiCl4, ethanol, Pluronic F-127, and 37% HCl in water, and (ii) ZnO solutions containing zinc acetate dihydrate, ethanol, Pluronic F-127, and 30% ammonium hydroxide dissolved in water.

Coating layer 12 is formed over D-shaped optical fiber 4 by dragging (e.g., manually) D-shaped optical fiber 4 through the precursor, immersed in an open dish, at a rate of approximately 1 cm/s. The coated sample is then exposed to a temperature treatment which includes initially drying the coated sample at 70° C., followed by a slow ramp of temperature to 130° C. and then to 600° C. to form the porous coating layer 12 (porous $SnO_2$ in the exemplary embodiment). Afterwards, the coated sample is allowed to cool down at a slow rate. Amongst the available choices of copolymers for porosity engineering at the nanoscale, poloxamer 407 (a triblock copolymer as noted above) is the most favored. Poloxamer 407 has been shown to provide highly porous $SnO_2$ coatings with average feature size of around 20 nm.

Figure 3A:
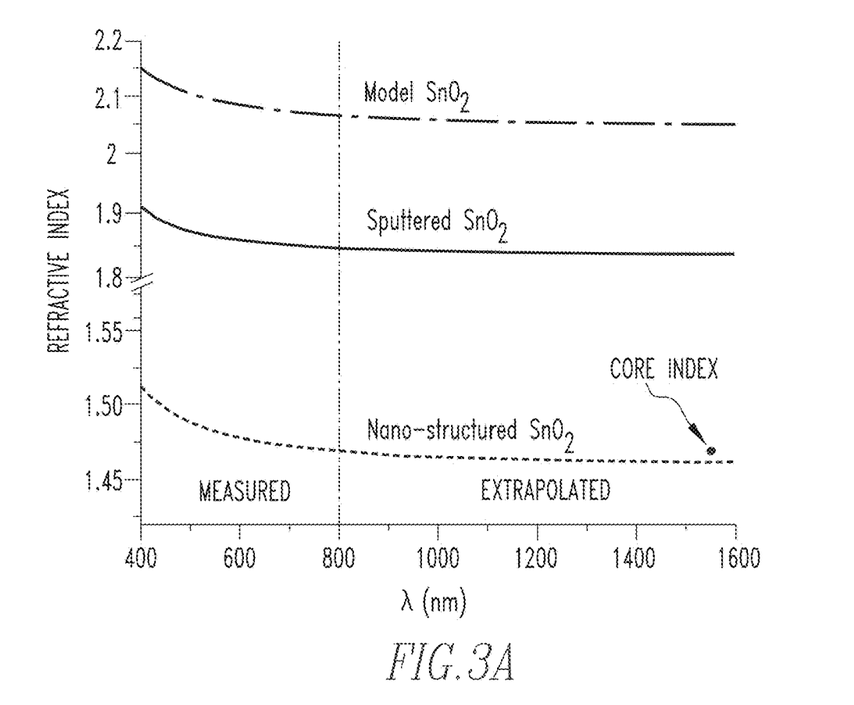
FIG. 3A is a graph showing the measured and extrapolated refractive indices of various forms of $SnO_2$ coatings prepared by an exemplary method of the present invention described herein.

FIG. 3A shows the measured (400-800 nm) and extrapolated (800-1600 nm) refractive indices of various forms of $SnO_2$ coatings prepared by the above described method according to one exemplary embodiment. The refractive index of bulk, fully dense $SnO_2$ is also presented as a reference. A 100 nm thick $SnO_2$ thin film prepared by sputter coating (estimated porosity of around 3-5%) is also included for comparison. Using the Lorentz single oscillator model with Bruggeman's Effective Medium Theory, it was determined that a volume fraction of about 60% void for the Nano-Structured $SnO_2$ was used. At 1550 nm, the wavelength of interest, it can be seen that the $SnO_2$ coating has a refractive index of 1.461, which is slightly smaller than the refractive index of the fiber core (1.468).

Figure 3B:
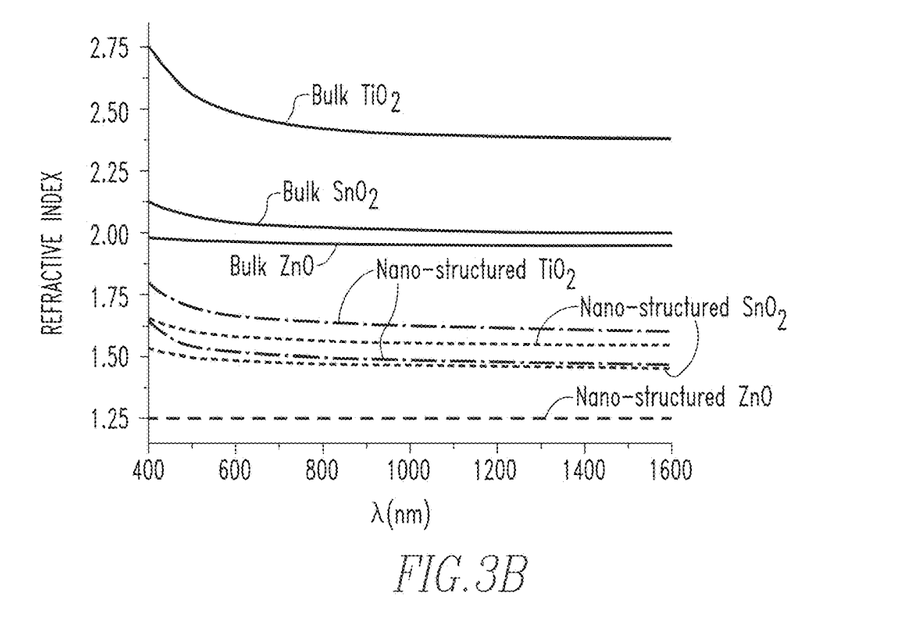
FIG. 3B is a graph showing the measured refractive indices of SnO2, TiO2 and ZnO coatings also prepared by an exemplary method of the present invention described herein.

FIG. 3B shows the measured refractive indices of various forms of SnO2 coatings prepared by the above described method and other metal oxides such as TiO2 and ZnO according to another exemplary embodiment. The refractive indices of their bulk, fully dense counterparts are also presented as a reference. Using the Lorentz single oscillator model with Bruggeman's Effective Medium Theory, a volume fraction of about 60% air void was determined for Nano-Structured SnO2 that was used to coat the fiber. At 1550 nm, the wavelength of interest, the SnO2 coating has a refractive index of 1.461, which is slightly smaller than the refractive index of the fiber core (1.468).

Figure 4A:
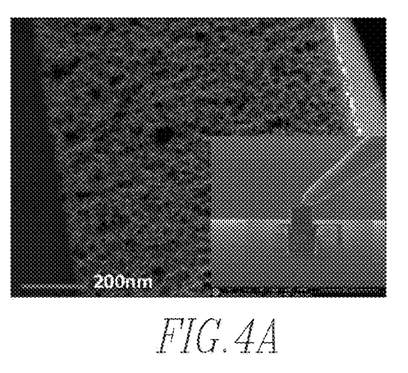
FIGS. 4A-4E show Transmission Electron Microscope (TEM) and Scanning Electron Microscope (SEM) images of exemplary fabricated nanostructures of which the TEM images for the $SnO_2$ nanomaterial were directly obtained from exemplary implementations of the fiber optic sensor device of FIGS. 1 and 2.
Figure 4B:
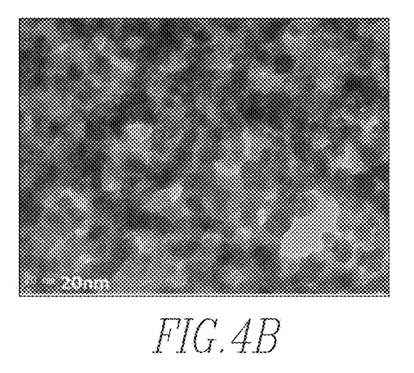
Figure 4C:
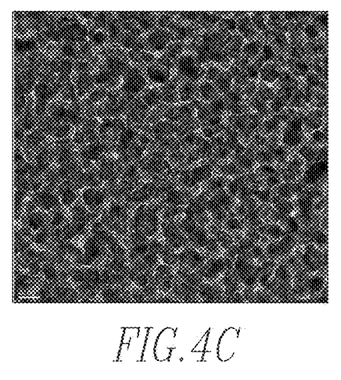
Figure 4D:
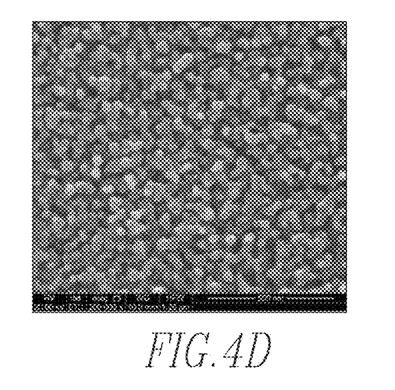
Figure 4E:
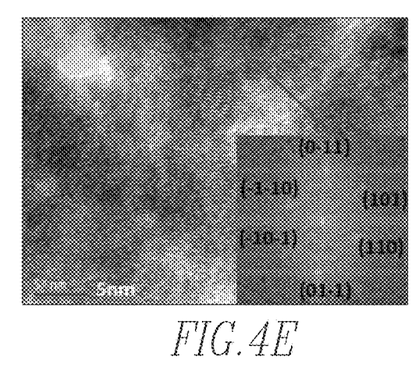

Moreover, in order to examine the underlying structure of the reduced index nanostructured metal oxide of the present invention, cross-sectional TEM samples were prepared using one particular exemplary embodiment of fiber optic sensor device 2 through standard FIB lift-out procedures. A protective layer of Pt was deposited on the surface prior to sectioning and a tungsten-probe tip was used for sample lift-out and electron transparency was obtained over an approximately 10 µm wide region for the entire film thickness. As expected, and a shown in FIG. 4A, the scanning transmission electron (STEM) image clearly shows a large degree of film porosity through z-contrast that is homogeneous over the entire region imaged with porosity features ranging from less than ~20 nm up to greater than ~50 nm in diameter. In addition, as shown in FIG. 4B, bright field TEM imaging shows an average $SnO_2$ grain size of approximately 10 nm. A Fast Fourier Transform (FFT) obtained from the high resolution TEM image confirms the expected cassiterite crystal structure, as shown in FIG. 4E. TEM imaging of a nanostructured TiO2 sample is presented in FIG. 4C. A scanning electron microscope image of an exemplary ZnO nanostructure is shown in FIG. 4D.

Figure 5:
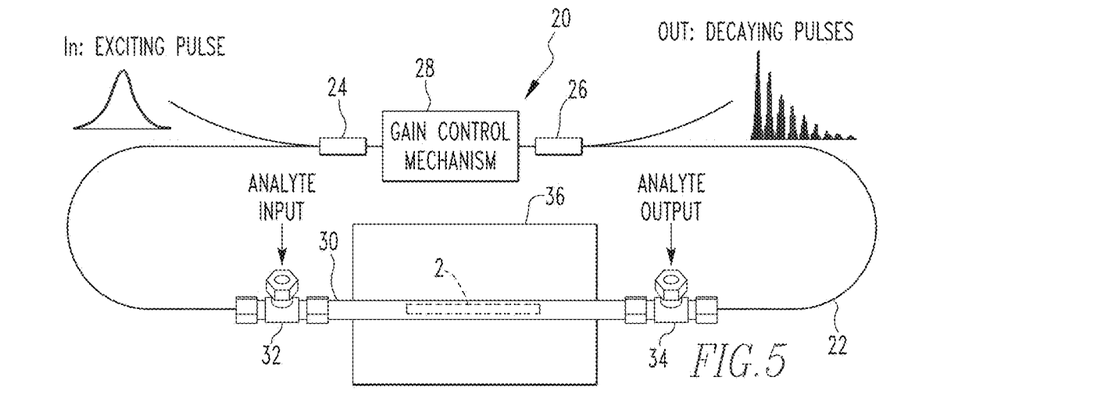
FIG. 5 is a schematic representation of a cavity ring down spectroscopy system which employs the fiber optic sensor device of FIGS. 1 and 2.

FIG. 5 shows one particular, exemplary application for fiber optic sensor device 2. More specifically, FIG. 5 is a schematic representation of a cavity ring down spectroscopy (CRDS) system 20 which employs fiber optic sensor device 2 for highly sensitive analyte detection. As is known in the art, CRDS is a highly sensitive optical spectroscopic technique that enables measurement of absolute optical extinction by samples that scatter and absorb light. It has been widely used to study gaseous samples which absorb light at specific wavelengths, and in turn to determine mole fractions down to the parts per trillion level.

Referring to FIG. 5, in the illustrated embodiment, CRDS system 20 includes an optical fiber 22 that is provided in the form of a circulating ring structure. In the exemplary embodiment, optical fiber 22 is a D-shaped optical fiber. A fiber coupler 24 is provided to enable an exciting pulse to be transmitted into optical fiber 22, and a fiber coupler 26 is provided to enable decaying pulses to be transmitted out of optical fiber 22 for analysis. Some gain control mechanism 28 is included between fiber coupler 24 and fiber coupler 26. The purpose of the gain control scheme is to minimize the intrinsic losses in the system prior to sensory analysis. The exemplified schematic is a simplified representation of a generally more complex system and does not exclude more elaborate cavity ring down schemes that may be used to exploit the adjusted refractive index integrated optical fiber. Cavity ring-down schemes with gain control mechanisms such as those described in Nicholas L. P. Andrews, "Near-infrared absorption detection in picoliter liquid volumes using amplified fibre loop ring-down detection", Optical Fiber Technology 19 (2013), pp. 822-827; George Stewart, "An investigation of an optical fibre amplifier loop for intra-cavity and ring-down cavity loss measurements", Measurement Science and Technology 12 (2001), pp. 843-849; Helen Waechter, "Chemical Sensing Using Fiber Cavity Ring-Down Spectroscopy", Sensors 2010, 10, pp. 1716-1742; and George Stewart, "Cavity-enhanced spectroscopy in fiber cavities", Optics Letters, Mar. 1, 2004, pp. 442-444, Vol. 29, No. 5. may be used to adjust and control gain in the loop to yield long ring-down decay time for sensitive chemical measurements.

CRDS system 20 further includes a quartz tube 30 having an analyte input end 32 and an analyte output end 34. A heating element 36 is provided around a portion of quartz tube 30.

Furthermore, as seen in FIG. 5, optical fiber 22 includes fiber optic sensor device 2 at a portion thereof that is located within quartz tube 30 and heating element 36. In the exemplary embodiment, fiber optic sensor device 2 is of the type that does not include an in-fiber optic component 10.

In operation, an analyte (e.g., a gas species) is introduced into quartz tube 30, and an exciting pulse is transmitted into optical fiber 22. The exciting pulse is circulated within the loop of optical fiber 22 many times (e.g., 1000 times). As will be appreciated, with each circulation, the exciting pulse will experience some loss. While the amount of loss in each circulation is small, that loss will accumulate over time with each circulation. Thus, during the circulation process, decaying pulses are transmitted out of optical fiber 22 and are used to analyze the analyte. For example, the time it takes the exciting pulse to decay to 1/e of its initial intensity (the "ringdown time") can be used to calculate the concentration of the analyte in quartz tube 30.

In addition, fiber optic sensor device 2 may also be used in a distributive fiber sensing application wherein the scattered light within a fiber is used for sensing purposes. As is known in the art, distributive fiber sensing can be broken down into two categories. The first is known as Brillouin scattering, which is realized by sending a high energy optical pulse into an optical waveguide. The lattice vibrations generated give rise to a pressure wave traveling at the speed of sound. This pressure wave can be considered as a moving grating along the fiber and its properties will depend on the surrounding environment. The returning probing light will carry information about this environment and can be used for detection. The second type of distributive sensing is known as Rayleigh scattering. Here, one measures the backscattered light which contains information as well about the fiber surroundings, such as refractive index variations, absorption losses, and etc.

Thus, in another exemplary application of fiber optic sensor device 2, such a device may be provided in an environment, such as a chemical plant, where it would be desirable to be able to detect the presence of a chemical species. In such an application, fiber optic sensor device 2 may have a relatively long length, e.g., 100 m, in order to cover the area of interest, and distributive fiber sensing as described above (Brillouin scattering or Rayleigh scattering) may be used to determine the location along fiber optic sensor device 2 where the chemical species is being absorbed, which may indicate a leak at that location.

Figure 6:
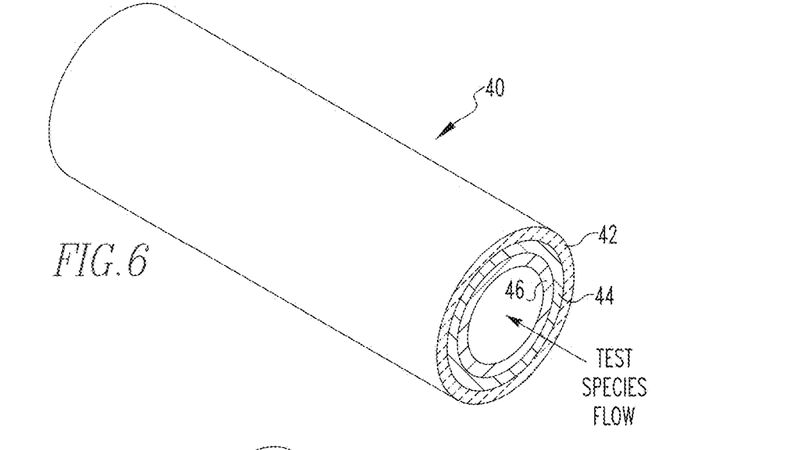
FIG. 6 is a schematic diagram of a fiber optic sensor device according to an alternative exemplary embodiment.

FIG. 6 is a schematic diagram of a fiber optic sensor device 40 according to an alternative exemplary embodiment. Fiber optic sensor device 40 is a multilayer hollow waveguide device that includes at least the following three layers: (i) a hollow waveguide tube layer 42 (e.g., cylindrical or other shape) made of a material such as silica, plastic, or metal such as nickel, (ii) a reflective coating layer 44 provided on an inner surface of hollow waveguide tube layer 42 and made of, for example, a metal material such as silver or gold, and (iii) a metal oxide coating layer 46 provided on an inner surface of reflective coating layer 44. In the exemplary embodiment, metal oxide coating layer 46 is engineered in refractive index and porosity on the 10-50 nm scale to increase the sensory sensitivity. In an alternative exemplary embodiment, metal oxide coating layer 46 has a reduced refractive index as described elsewhere herein such that it is less than that of silica (e.g., the refractive index of hollow waveguide tube layer 42). In fiber optic sensor device 40, an interrogating light can be confined by either waveguiding (via total internal reflection) or by pure reflection off of reflective coating layer 44. By providing metal oxide coating layer 46 on the inside of waveguide tube layer 42 and reflective coating layer 44, more light (as compared to fiber optic sensor device 2) will propagate inside metal oxide coating layer 46, thereby leading to enhanced sensitivity. Fiber optic sensor device 40 may also include one or more layers in addition to those just described. For example, a protective dielectric coating may be provided on either or both sides (i.e., inner/outer) of reflective coating layer 44. In addition, a multilayered metal oxide sensing layer may be employed for improved selectivity or optimized response. Fiber optic sensor device 40 may, in one exemplary implementation, be employed in CRDS system 20 in place of fiber optic sensor device 2.

Figure 7:
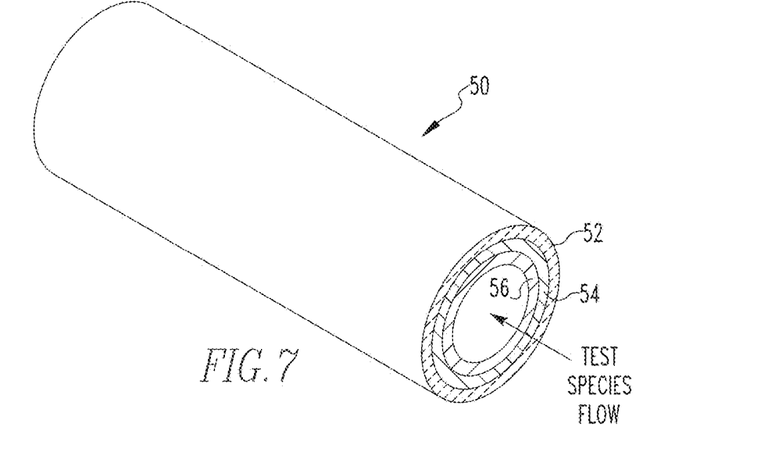
FIG. 7 is a schematic diagram of a fiber optic sensor device according to another alternative exemplary embodiment.

FIG. 7 is a schematic diagram of a fiber optic sensor device 50 according to an alternative exemplary embodiment. Fiber optic sensor device 50 is also a multilayer hollow waveguide device that includes at least the following three layers: (i) a hollow waveguide tube layer 52 (e.g., cylindrical or other shape) made of a material such as silica, plastic, or metal such as nickel, (ii) a high index guiding layer 54 provided on an inner surface of hollow waveguide tube layer 52 and made of, for example, glass or dielectric material such as, without limitation, $Al_2O_3$ or $ZrO_2$, and (iii) a metal oxide coating layer 56 provided on an inner surface of guiding layer 54. In the exemplary embodiment, guiding layer 54 has an index of refraction that is higher than the index of refraction of hollow waveguide tube layer 52. In the exemplary embodiment, metal oxide coating layer 56 is structured to have a reduced refractive index as described elsewhere herein (e.g., it is a nanostructure material) such that it has a refractive index that is less than the index of refraction of guiding layer 54. Fiber optic sensor device 50 may also include one or more layers in addition to those just described. Fiber optic sensor device 50 may, in one exemplary implementation, be employed in CRDS system 20 in place of fiber optic sensor device 2.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of sensing an analyte in an environment in a spatially distributed manner, comprising:

providing an optical sensor device in the environment, the optical sensor device including an optical waveguide portion having a core, the core having a first refractive index, and a functional material layer coupled to the optical waveguide portion, the functional material layer being comprised of a material that in a bulk, fully dense form has a natural, non-engineered refractive index that is greater than the first refractive index, the functional material layer being structured to have an engineered second refractive index that is lower than the first refractive index, wherein the functional material layer is an engineered nanostructure material with a plurality of voids formed therein, wherein throughout the functional material layer a porosity of the functional material layer is uniform and a size and a shape of the voids is uniform such that the functional material layer is caused to have the engineered second refractive index and such that light scattering in the optical sensor device is minimized, wherein the functional material layer is a material wherein at least one of the engineered second refractive index of the functional material layer or the optical absorption of the functional material layer will change in response to a parameter relating to the analyte, and wherein the engineered second refractive index of the functional material layer and losses thereof are engineered as to permit interrogation of a desired length of the optical sensor device or a plurality of sensing locations along the optical sensor device using a spatially distributed sensing technique without employing a plurality of in-fiber optic components in the core of the optical sensor device; and sensing a presence of or measuring the parameter relating to the analyte at a plurality of locations along the optical sensor device using the spatially distributed sensing technique without employing a plurality of in-fiber optic components in the core of the optical sensor device.

2. The method according to claim 1, wherein the spatially distributed sensing technique without employing a plurality of in-fiber optic components in the core of the optical sensor device comprises Brillouin scattering or Rayleigh scattering.

3. The method according to claim 1, wherein the functional material layer is provided on a surface of the optical waveguide portion.

4. The method according to claim 3, wherein the optical waveguide portion is a D-shaped optical fiber having a cladding layer having a partial cylindrical cross-section, the cladding layer and the functional material layer being made of different materials, the core being provided at least in part within the cladding layer and being partially exposed to the environment, the functional material layer being provided on a top, flat surface of the cladding layer and a top portion of the core.

5. The method according to claim 1, wherein the voids comprise about 60% of the nanostructure material causing the functional material layer to have a total volume fraction of voids of about 60%.

6. The method according to claim 1, wherein the voids each have a width or diameter of 50 nm or less, and wherein the voids comprise about 60% of the nanostructure material causing the functional material layer to have a total volume fraction of voids of about 60%.

7. The method according to claim 6, wherein the voids each have a width or diameter of about 10 nm to about 20 nm.

8. The method according to claim 1, wherein the engineered second refractive index is about 99.0% to about up to 99.7% of the first refractive index.

9. The method according to claim 1, wherein the nanostructure material is formed using a sol-gel method.

10. The method according to claim 9, wherein the sol-gel method uses a block copolymer as a structure directing agent.

11. The method according to claim 10, wherein the block copolymer is a triblock copolymer and is poloxamer 407.

12. The method according to claim 1, wherein the material comprising the functional material layer is selected from a group consisting of a zeolite, $SnO_2$, $TiO_2$, ZnO, $WO_3$, and a perovskite.

13. A method of sensing an analyte in an environment in a spatially distributed manner, comprising:
providing an optical waveguide portion having a core, the core having a first refractive index, and a functional material layer coupled to the optical waveguide portion, the functional material layer being structured to have an engineered second refractive index that is lower than the first refractive index, wherein the functional material layer is an engineered nanostructure material with a plurality of voids formed therein, wherein throughout the functional material layer a porosity of the functional material layer is uniform and a size and a shape of the voids is uniform such that the functional material layer is caused to have the engineered second refractive index and such that light scattering in the optical sensor device is minimized, and wherein the functional material layer is a material wherein at least one of the engineered second refractive index of the functional material layer or the optical absorption of the functional material layer will change in response to a parameter relating to the analyte, and wherein the engineered second refractive index of the functional material layer and losses thereof are engineered as to permit interrogation of a desired length of the optical sensor device or a plurality of sensing locations along the optical sensor device using a spatially distributed sensing technique without employing a plurality of in-fiber optic components in the core of the optical sensor device; and
sensing a presence of or measuring the parameter relating to the analyte at a plurality of locations along the optical sensor device using the spatially distributed sensing technique without employing a plurality of in-fiber optic components in the core of the optical sensor device.

14. The method according to claim 13, wherein the spatially distributed sensing technique without employing a plurality of in-fiber optic components in the core of the optical sensor device comprises one of Brillouin scattering or Rayleigh scattering.

* * * * *